United States Patent [19]

Mueller

[11] Patent Number: 5,167,652

[45] Date of Patent: Dec. 1, 1992

[54] MOISTURE SENSITIVE FILM

[75] Inventor: Walter B. Mueller, Inman, S.C.

[73] Assignee: W. R. Grace & Co.-Conn., Duncan, S.C.

[21] Appl. No.: 303,432

[22] Filed: Jan. 27, 1989

[51] Int. Cl.$^5$ .............................. A61F 13/15
[52] U.S. Cl. .................................... 604/385.1
[58] Field of Search .................. 604/365, 385, 361

[56] References Cited

U.S. PATENT DOCUMENTS

| | | | |
|---|---|---|---|
| 4,231,370 | 11/1980 | Mroz et al. | 128/287 |
| 4,681,576 | 7/1987 | Colon et al. | 604/361 |
| 4,895,567 | 1/1990 | Colon et al. | 604/365 |

*Primary Examiner*—David Isabella
*Attorney, Agent, or Firm*—William D. Lee, Jr.; Jennifer L. Skord; Mark B. Quatt

[57] ABSTRACT

A moisture sensitive film is produced by blending a copolyester with a moisture absorbing copolyamide, and extruding the blend either as a mono layer or multi layer construction. The blend material turns white when wetted. The invention has particular application in disposable diapers where a visual indication of wetness is desired.

2 Claims, 1 Drawing Sheet

MOISTURE SENSITIVE FILM

FIELD OF THE INVENTION

The present invention relates to thermoplastic film, and more particularly to thermoplastic film useful in the construction of disposable diapers. The present invention is of especial relevance to thermoplastic films which provide a visual indication of the presence of moisture in a disposable diaper or similar article.

BACKGROUND OF THE INVENTION

Disposable diapers have to a great extent replaced cloth diapers in the field of infant care. Many different styles of disposable diapers have been introduced to the marketplace, differing in materials, physical configuration, and cost.

One recurrent problem associated with the use of disposable diapers is the inability to quickly and conveniently determine when the diaper is wetted during use.

Various methods have been offered to provide wetness indicators in a disposable diaper. For example, U.S. Pat. No. 4,231,370 (Mroz et al) discusses the application of a flexible pH-change/color-change wetness indicator coating on the inwardly facing surface of a water-impervious thermoplastic backsheet of a disposable diaper. This approach has the disadvantage of requiring a separate coating material to be applied in an additional step. The preferred coating material itself is a complex four-component composition of two latex compositions, an acid buffer, and a pH-change/color-change material such as bromophenol blue. The mixing of these components is a long, complex process.

U.S. Pat. No. 4,611,576 (Colon) discloses a wetness-indicating hot-melt adhesive for a diaper. The adhesive composition includes water sensitive polymer and optional additional polymer resins; fatty acid with optionally an additional organic acid; optionally a water soluble wax; and a wetness indicating agent such as acid-base indicators. Like the '370 reference, this reference requires a complicated formulation to be prepared prior to production of the diaper. The adhesive product is applied to a substrate.

It is an object of the present invention to provide a thermoplastic film which is useful as a cover or backing sheet in a disposable diaper, and will change color when wet.

SUMMARY OF INVENTION

In one aspect of the invention, a thermoplastic film which changes color when wetted comprises a blend of a copolyester, and a moisture absorbing copolyamide.

In another apsect of the invention a thermoplastic film comprises a core layer of ethylene vinyl alcohol copolymer, a first outer layer of a copolyester, a second outer layer of a blend of a copolyester and a moisture absorbing copolyamide, and a polymeric adhesive disposed between and bonding the core layer to the first outer layer, and the core layer to the second outer layer, respectively.

In another aspect of the invention, a method of making a thermoplastic film which changes color when wetted comprises blending a copolyester with a moisture absorbing copolyamide; extruding the blend; and cooling the extrudate.

In yet another aspect of the present invention, a disposable diaper has at least one layer comprising a blend of a copolyester and a moisture absorbing copolyamide.

In still another aspect of the invention, a composition of matter comprises a blend of a copolyester and a moisture absorbing copolyamide.

BRIEF DESCRIPTION OF THE DRAWING

The invention may be further understood by reference to the sole drawing FIGURE which depicts a schematic cross section of a disposable diaper in accordance with the present invention.

DESCRIPTION OF THE PREFERRED EMBODIMENT

Figure 1:
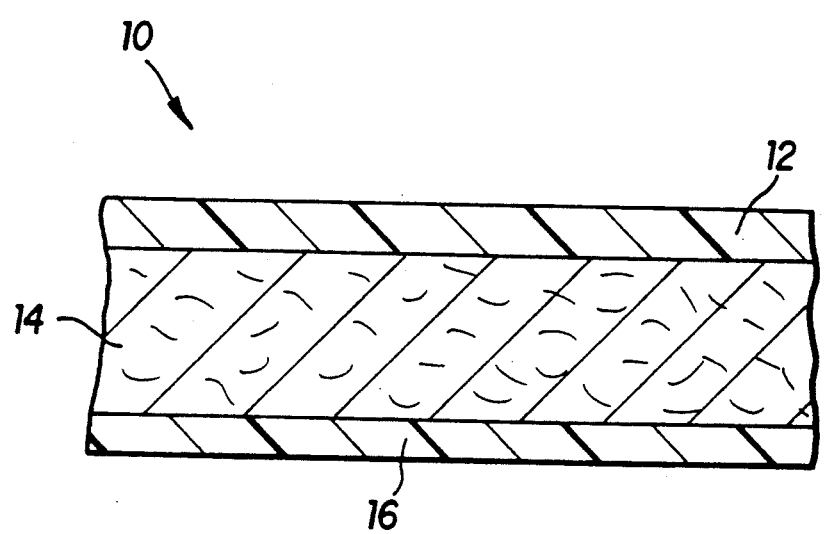

Referring to the sole drawing FIGURE, disposable diaper 10 comprises an inner sheet 12 of a moisture permeable or perforated material.

An intermediate layer 14, generally making up the greater thickness of the diaper 10, comprises an absorbant material such as cellulosic fluff or a synthetic moisture absorbing polymer.

The cover or backing sheet 16 forms the outermost layer of the diaper. In accordance with the invention, layer 16 comprises a blend of a copolyester and a moisture absorbing copolyamide. It has unexpectedly been found that when this blend is exposed to moisture, the originally transparent blend turns white. This process is reversible, so that the dissipation of moisture from the blend layer and drying out of the blend material will result in the return of the whitened material to a transparent state.

Thus, a blend material which may be conveniently incorporated into the construction of the diaper is provided which gives a clear visual indication of when the diaper is wet.

The complex precompounding of the prior art is unnecessary. A simple blending of two commercially available resins provides the visual indicator which becomes an integral part of the diaper construction.

Coatings and adhesives to be applied to a substrate are also unnecessary.

Additionally, the visual indication of wetness does not depend on the reaction of a pH/color indicator, and no such indicator is needed. The use of potentially harmful acids such as phosphoric acid is also avoided.

The invention may be further understood by reference to the following table, in which various formulations were tested.

Each of film samples 1, 4, 6, 7, and 8 were coextruded structures having the generalized structure:

A/B/C/B/E

Where
- A = PCCE 9965 (a copolyester available from Eastman)
- B = CXAE162 (an EVA based anhydride modified adhesive available from du Pont); and
- C = 5192B7-9 (an ethylene vinyl alcohol copolymer available from du Pont).

In addition, a second set of monolayer film samples 1 to 5 was produced to confirm the results obtained by observation of the first set of film samples. This monolayer film may be described as having the simple construction /E/. The monolayer film results were consistent with those obtained by using the same formulation in the "E" layer of the corresponding A/B/C/B/E coextruded film. This establishes that the results (degree of color change) are substantially independent of the composition of the other (A, B, C) layers in the coextruded film.

The results of the first set of film samples are shown under the column labeled "coextrusion" in Table 1. The results of the second set of film samples are shown under the column labeled "monolayer" in Table 1.

Table 1 has a column labeled "E Layer".

For film samples 2, 3 and 5 the composition listed under this heading represents that of a monolayer film.

For film samples 6, 7, and 8 the composition listed under this heading represents that of the outer "E" layer of the five layer coextrusion.

For film samples 1 and 4, the composition listed under this heading represents both that of the outer "E" layer of the five layer coextrusion, as well as that of a monolayer film.

Film 1 100% water absorbing copolyamide (PEBAX 4011)
Film 2 95% water absorbing copolyamide plus 5% copolyester (95% Pebax 4011 and 5% PCCE 9965)
Film 3 85% water absorbing copolyamide plus 15% copolyester (85% Pebax 4011 and 15% PCCE 9965)
Film 4 75% water absorbing copolyamide and 25% copolyester (75% PEBAX 4011 and 25% PCCE 9965)
Film 5 60% water absorbing copolyamide plus 40% copolyester (60% Pebax 4011 and 40% PCCE 9965)
Film 6 50% water absorbing copolyamide and 50% copolyester (50% PEBAX 4011 and 50% PCCE 9965)
Film 7 25% water absorbing copolyamide plus 75% copolyester (25% PEBAX 4011 and 75% PCCE 9965)
Film 8 100% copolyester (PCCE 9965)

TABLE 1

| Film | "E" Layer | Color After Exposure To Direct Contact With Moisture | |
|---|---|---|---|
| | | Coextrusion | Mono-Layer |
| 1 | 100% Copolyamide | Clear | Clear |
| 2 | 95% Copolyamide +5% Copolyester | | Pale White |
| 3 | 85% Copolyamide +15% Copolyester | | White |
| 4 | 75% Copolyamide +25% Copolyester | White | White |
| 5 | 60% Copolyamide +40% Copolyester | | White |
| 6 | 50% Copolyamide +50% Copolyester | Pale White | |
| 7 | 25% Copolyamide +75% Copolyester | Clear | |
| 8 | 100% Copolyester | Clear | |

While not wishing to be held to any particular theory, it is believed that as the moisture absorbing copolyamide absorbs water, the copolyamide swells resulting in blend incompatibility which manifests itself by turning a white opaque color. The process is reversible.

In an alternative embodiment, a portion of the diaper may be printed with a pattern, perforated and laminated to the moisture sensitive layer 16. If this additional laminate has a white color, then the printed pattern will disappear when the diaper becomes wet.

Those skilled in the art will understand that this and other modifications and applications may be made without departing from the spirit and scope of the invention as claimed below.

What is claimed is:

1. A thermoplastic film comprising:
   (a) a core layer of ethylene vinyl alcohol copolymer;
   (b) a first outer layer of a copolyester;
   (c) a second outer layer of a blend of a copolyester and a moisture absorbing copolyamide; and
   (d) a polymeric adhesive disposed between and bonding the core layer to the first outer layer, and the core layer to the second outer layer, respectively.

2. A disposable diaper having an outermost layer comprising a blend of between 5% and 50% by weight of a copolyester and 95% and 50% by weight of a moisture absorbing copolyamide; an intermediate layer comprising an absorbant material; and an inner sheet comprising a moisture permeable or perforated material.

* * * * *